United States Patent
Schröder et al.

(10) Patent No.: US 7,056,431 B2
(45) Date of Patent: Jun. 6, 2006

(54) METHOD FOR ELECTROCHEMICAL ANALYSES

(76) Inventors: Knut Schröder, Vilhelm Krags vei 2, N-7023, Trondheim (NO); Öyvind Mikkelsen, Myrsnipeveien 20, N-7082, Kattem (NO)

( * ) Notice: Subject to any disclaimer, the term of this patent is extended or adjusted under 35 U.S.C. 154(b) by 237 days.

(21) Appl. No.: 10/257,443

(22) PCT Filed: Apr. 9, 2001

(86) PCT No.: PCT/NO01/00155

§ 371 (c)(1),
(2), (4) Date: Aug. 19, 2003

(87) PCT Pub. No.: WO01/80328

PCT Pub. Date: Oct. 25, 2001

(65) Prior Publication Data

US 2004/0020792 A1    Feb. 5, 2004

(51) Int. Cl.
*G01N 27/333* (2006.01)
(52) U.S. Cl. ............................ 205/789; 205/775
(58) Field of Classification Search ........ 204/416–420, 204/431, 403.01, 400, 280, 291, 292, 293; 205/775, 789, 794.5
See application file for complete search history.

(56) References Cited

U.S. PATENT DOCUMENTS

| 4,211,623 A | 7/1980 | Ross, Jr. et al. ............ 204/419 |
| 5,672,257 A | 9/1997 | Birch et al. .................... 205/43 |

FOREIGN PATENT DOCUMENTS

| JP | 59-217154 A | * 12/1984 |
| JP | 60-73450 A | * 4/1985 |
| JP | 5-126783 | 5/1993 |
| RO | 111807 | 1/1997 |
| SU | 1002943 | 3/1983 |

OTHER PUBLICATIONS

Scandinavian Journal of Dental Research (1986), 94(3), 259-66.*
JPO computer translation of Noriyasu et al. (JP 5-126783 A).*
page 2:156 of Corrosion:vol. 1 Metal/Environment Reactions ed. Shreir et al., Butterworth-Heinemann 2000.*
JPO abstract of Oodo et al. (JP 60-73450 A).*
JPO abstract of Tanaka et al. (JP 59-217154 A).*
pages 171-172 of the Guide to dental materials and devices, seventh edition American Dental Association.*
English language translation of JP 60-73450 A.*
English language translation of JP 59-217154 A.*
CAPLUS abstract for RO 11807 B3.*

* cited by examiner

*Primary Examiner*—Alex Noguerola
(74) *Attorney, Agent, or Firm*—Wenderoth, Lind & Ponack, L.L.P.

(57) ABSTRACT

Dental amalgam as an electrode material in voltammetry is provided having a very high overpotential to hydrogen. Accordingly, trace analyses can be carried out at potentials sufficiently negative to allow determination of e.g. zinc, cobalt, nickel and iron at trace levels. Such analyses have not previously been possible except by using a mercury or a mercury film electrode. Such determinations are very important for field and online analyses of pollutants in soil and groundwater, and the electrode can be used repeatedly.

8 Claims, 6 Drawing Sheets

METHOD FOR ELECTROCHEMICAL ANALYSES

This application claims priority under 35 U.S.C. 371 from PCT/NO01/00155, which was filed on Apr. 9, 2001.

BACKGROUND OF THE INVENTION

The present invention relates to an electrode for use in electrochemical analysis.

Since the development of polarography by Professor J. Heyrovsky in 1922, liquid mercury and liquid diluted mercury amalgams have been superior as an electrode material for the use of voltammetry for analytical purposes. This is mainly due to the high overvoltage to hydrogen, which enables the use of a wide potential range for the measurements. A typical example is the determination of zinc, this being virtually impossible without using a mercury; or a mercury film electrode.

Due to the toxicity of mercury and liquid diluted mercury compounds, the use of such compounds is increasingly restricted, and cannot be included in voltammetric devices for field and online applications.

SUMMARY OF THE INVENTION

The properties of dental amalgam as an electrode material in voltammetry have been studied. It was found that dental amalgam has a very high overpotential to hydrogen, allowing trace analyses to be carried out at potentials sufficiently negative to allow determination of e.g. zinc, cobalt, nickel and iron at trace levels. This has not previously been possible except by using a mercury or a mercury film electrode. Such determinations are very important for field and online analyses of pollutants in soil and groundwater, and the electrode can be used repeatedly. The electrode is also solid.

Silver and mercury are the main components of dental amalgam. However, commercial dental alloy has some tin, copper and zinc content in order to improve the mechanical properties for dental use. A pure silver amalgam can be used to avoid interferences.

The electrodes can be produced using techniques well established in dental practice.

Due to the special properties of dental amalgam compared with mercury itself, its toxicity is very low, although its use in the mouth is somewhat disputed. As no increased amount of mercury is reported in the groundwater close to cemeteries, the use of such small electrodes for soil and groundwater analyses are obviously without any hazard.

The present analyses describe such electrodes and some preliminary practical applications for trace heavy metal analyses, using differential pulse stripping voltammetry. This enables the determination of, for example, zinc in the concentration level less than 10 ppb. Further improvements can obviously be obtained by optimizing the composition of the alloy and the electrolyte, and by the application of sound to the electrode system. (Application of sound to an electrode system is described in the inventors' Norwegian patent application number 1999 1814.)

In a first aspect of the present invention there is provided an electrode for use in electrochemical analysis, where the electrode comprises amalgam in a solid state.

In a second aspect of the invention there is provided a means for performing electrochemical analyses involving a redox reaction at an electrode surface, comprising an analysis cell, a system of electrodes arranged in the analysis cell filled with a solution to be analyzed through production of a measuring signal as a consequence of a redox reaction at the electrodes, wherein the measuring signal is a measure of the concentration of a component in the solution, and where at least one of the electrodes comprises amalgam in a solid state.

The amalgam may be any solid amalgam to be approved to be at least in the same environmental safety level as the requirements for dental use. The electrode may be in the form of a ceramic rod enclosing the amalgam, and with a copper wire for electrical connection. The amalgam in the electrode may be made using methods familiar in dental techniques.

The electrode may be used as a measuring electrode in voltammetric analysis, especially differential pulse anodic stripping voltammetry.

The invention is stated in the appended claims.

BRIEF DESCRIPTION OF THE DRAWINGS

Embodiments of the invention will now be described in the following with reference to the accompanying drawings, where.

DETAILED DESCRIPTION OF THE INVENTION

A. Experimental

Figure 1:
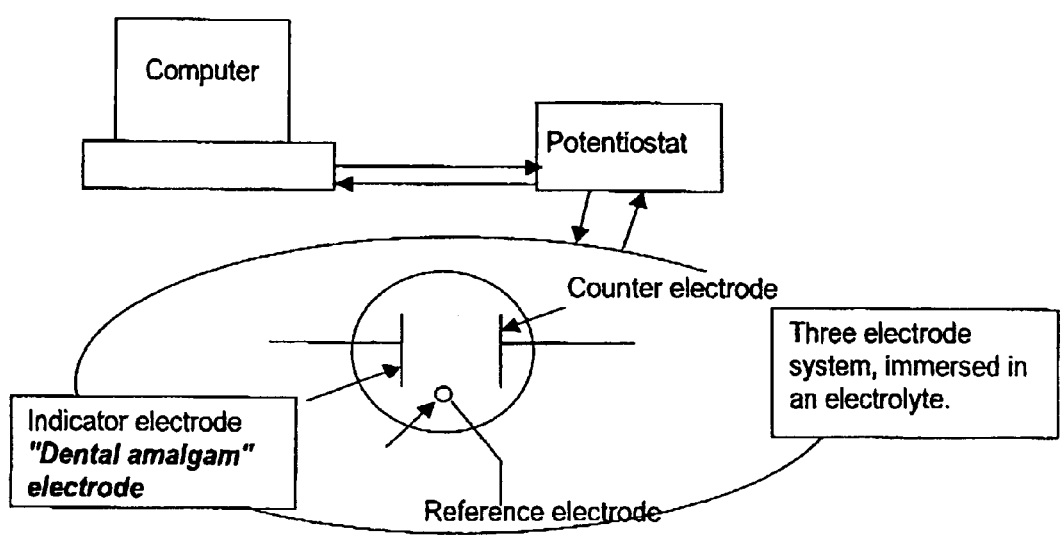
FIG. 1 shows a three-electrode system.

The analyses were performed as differential pulse anodic stripping voltammetry, using a three-electrode system as shown in FIG. 1. The three electrodes in FIG. 1 are an indicator electrode, which is the dental amalgam electrode, a counter electrode and a reference electrode. The three-electrode system is immersed in an electrolyte. The three-electrode system is connected to a potentiostat. The potentiostat is connected to a computer. The voltammetric equipment is a digital device that can perform all modes of voltammetry.

The counter electrode was a platinum wire and potentials were measured vs. a silver/silver chloride/saturated silver chloride/saturated potassium chloride reference electrode.

Figure 2:
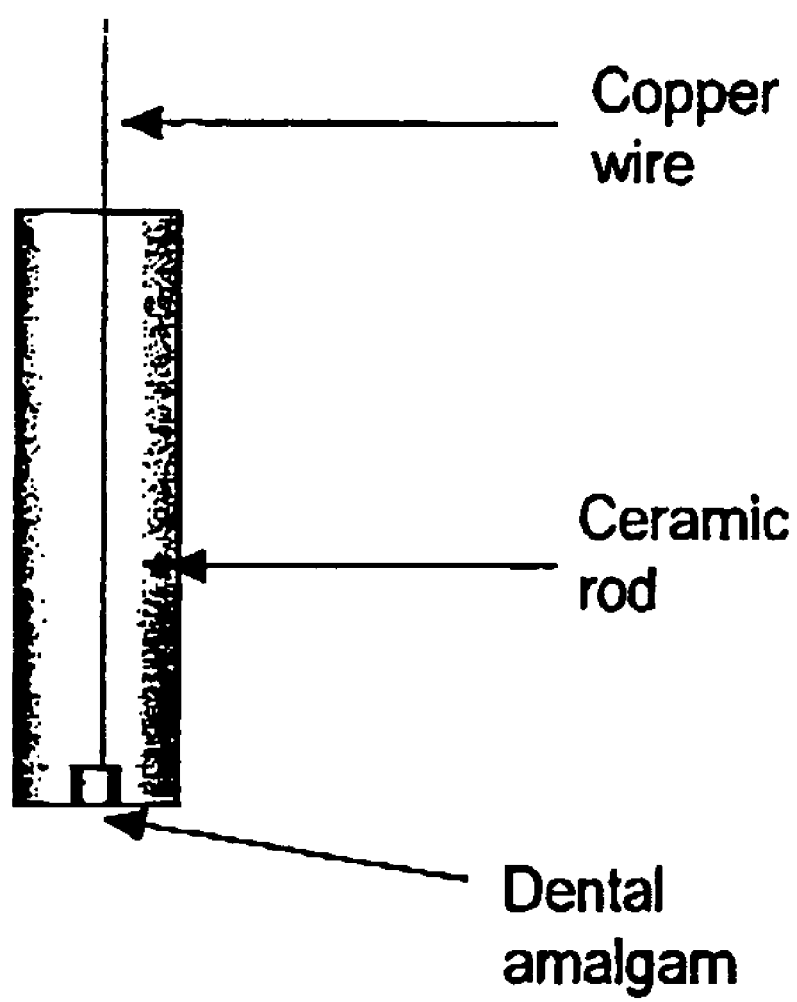
FIG. 2 is a cross-sectional view of a solid electrode according to an embodiment of the invention.

The working electrode was a silver amalgam electrode as illustrated in FIG. 2. Three types of dental amalgams were investigated:

1. The initial experiments were performed by using an amalgam tooth filling about 30 years old, which was attached to a copper wire with silver epoxy, the than sealed in cernit (from T+F GmbH). The copper wire was connected to the voltammetric equipment. These experiments were carried out to study if the dental amalgam showed overpotential to hydrogen. The analyses were performed by differential pulse anodic stripping voltammetry in $KNO_3$ (0.1 M, 100 ml) solution that was purged with nitrogen (10 min) prior to the analyses.

2. The second silver amalgam electrode was prepared by the following procedure using the facilities in a dental clinic: Equal amounts of analytical grade mercury were mixed with high copper non-gamma 2-alloy for dental use (ARDENT FUTURA, AB Ardent, Märsta Sweden). The non-gamma 2 alloy consists of 44.5% silver, 30.0% tin and 25.5% copper. A Dentomat 2 Degussa amalgam mixer for dental use was employed for mixing the amalgam. The amalgam was forced into an inert ceramic rod by an amalgam gun (No. 940, Hawe Neos Dental), in a way similar to the technique used for dental fillings, and sealed around a copper wire as shown in FIG. 2. The copper wire was connected to the voltammetric equipment. The experiments using this electrode were carried out to prove if it was possible to detect zinc at a non-zinc dental amalgam electrode. If it was found that zinc could be deposited and detected voltammetrically by using this electrode, this would also indicate that other heavy metals could be detected by use of a pure silver dental amalgam. The analyses were performed as differential pulse anodic stripping voltammetry in $NH_4Ac$ (0.05 M, 100 ml) solution. The solution was purged with nitrogen (10 min) prior to the analyses to avoid any disturbance of oxygen.

3. The third silver amalgam electrode was prepared by mixing one part of pure silver crystals for dental use (particle<50µ) with 0.65 parts analytical grade mercury, using a mortar. Immediately after mixing the amalgam was pressed into a ceramic rod with an amalgam gun as described above. Analyses were performed by differential pulse anodic stripping voltammetry in $NH_4Ac$ (0.05 M, 100 ml). These analyses were done to prove if it was possible to detect heavy metals, for instance zinc, cadmium and lead, on the dental amalgam electrode using a silver amalgam free from impurities like copper and zinc.

The three types of working electrodes were polished once before the experiments using a fine soften sandpaper, and washed in water purified by Millipore Elix and then with Millipore Milli-Q Gradient system (Millipore Corporation, SA 67120 Molsheim France). Also standard solutions were made by use of water from this water purification system. All reagents were of analytical reagent grade quality.

B. Results

The results will be divided into three sections, dealing with the respective working electrode used.

1. Initial results from using the 30 year old tooth filling as a working electrode.

Figure 3:
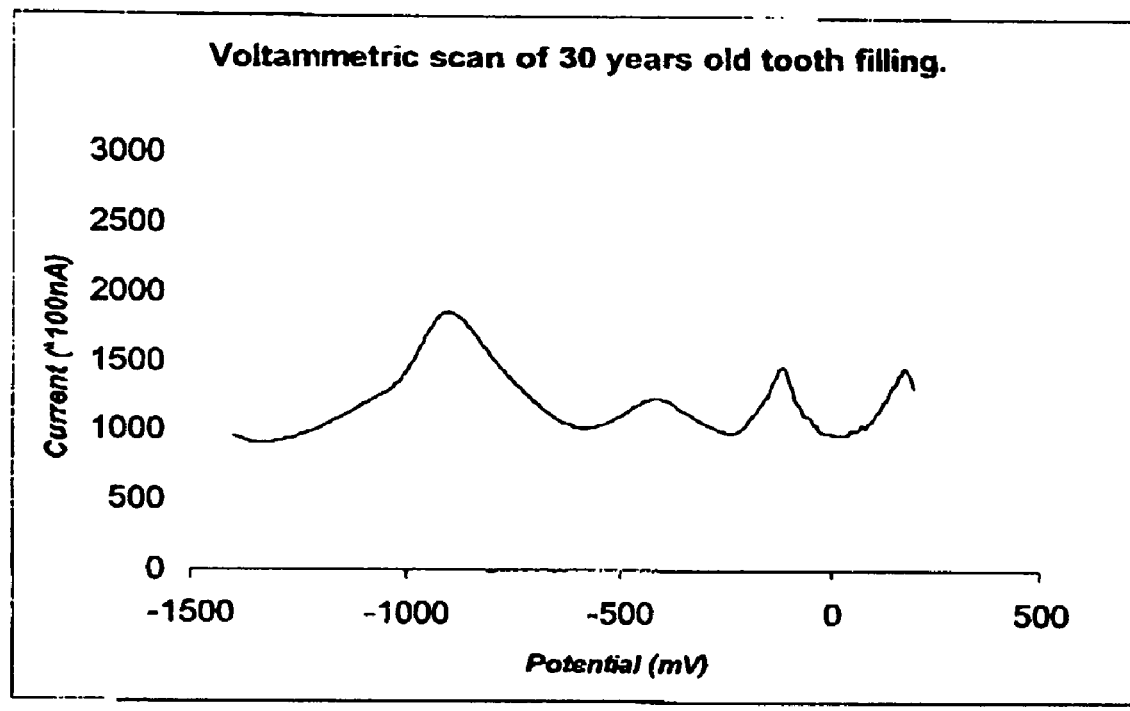
FIG. 3 is a graph showing a voltammetric scan of a 30 years old tooth filling in $KNO_3$ (0.1M) solution.

Some voltammetric scans were performed initially to find if the dental amalgam showed overvoltage to hydrogen to allow the use of a wide potential range. As explained under the experimental section, a thirty year old tooth filling was used as a working electrode in a voltammetric arrangement. The typical voltammogram obtained in a $KNO_3$ (0.1 M, 100 ml) solution is shown in FIG. 3. The voltammetric scan in FIG. 3 shows current (100 nA) as a function of potential (mV) and was performed with a scan rate of 10 mV/sec and pulse height 25 mV.

As shown in FIG. 3, the dental amalgam possess the property of a greater overvoltage against hydrogen. The peaks observed are reflecting the composition of the tooth filling, presumably corresponding to zinc, tin, copper and silver, from left to right. If the scan had been extended to around +300 mV, a peak for mercury would probably also appear.

2. Results from analyses using a non-zinc (high copper non-gamma 2-alloy) amalgam for dental use as a working electrode.

Analyses in order to prove if it was possible to detect heavy meals on an electrode consisting of a non-zinc (high copper non-gamma 2-alloy) amalgam for dental use was performed. Analyses of zinc in the range from 100 µg/l to 1500 µg/l in $NH_4Ac$ (0.05 M) solution was carried out. Differential pulse anodic stripping voltammetry with a scan rate of 10 mV/sec, pulse height 70 mV, and a 120 seconds deposition time was used.

Figure 4:
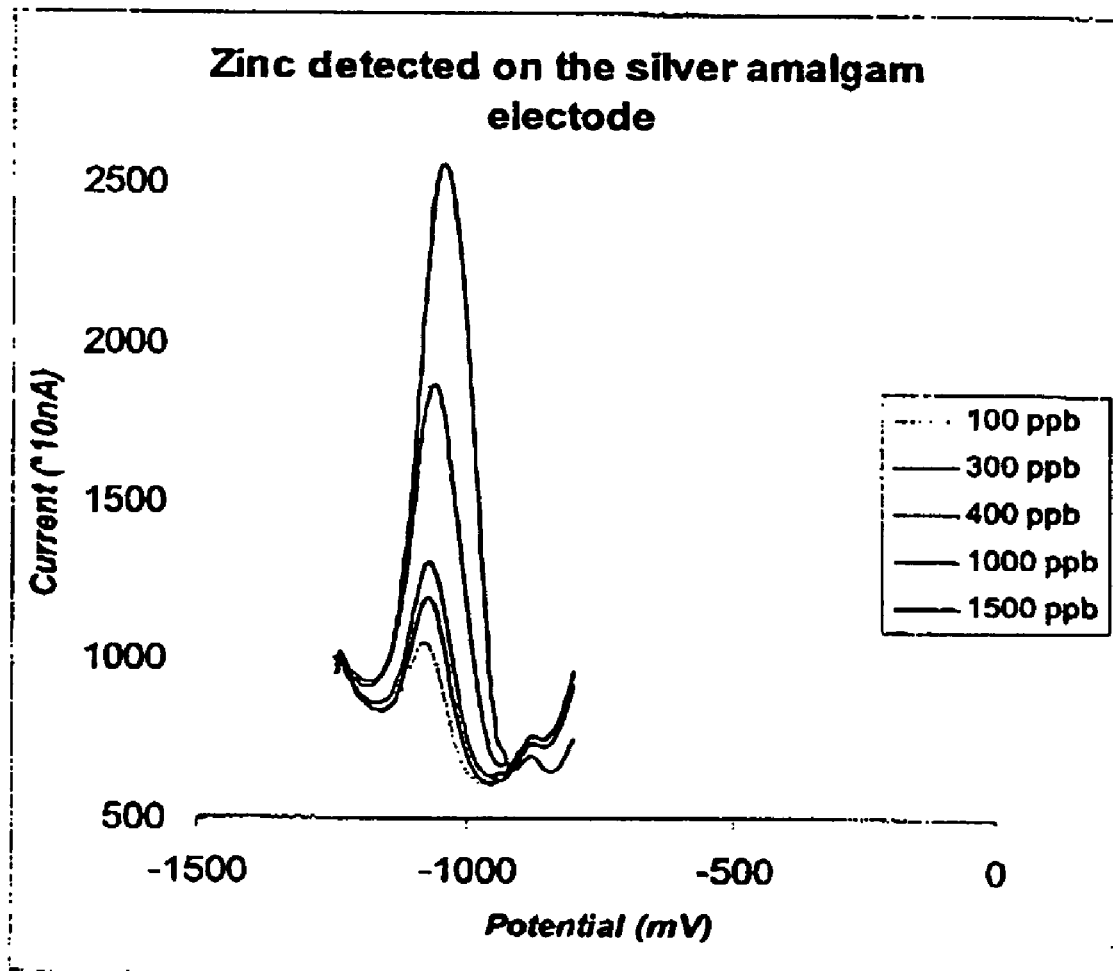
FIG. 4 is a voltammogram showing the detection of zinc on a working electrode containing a non-zinc amalgam for dental use.

FIG. 4 shows a voltammogram were zinc was added successively to the $NH_4Ac$ solution. In FIG. 4, current (100 nA) is shown versus potential (mV).

Figure 5:
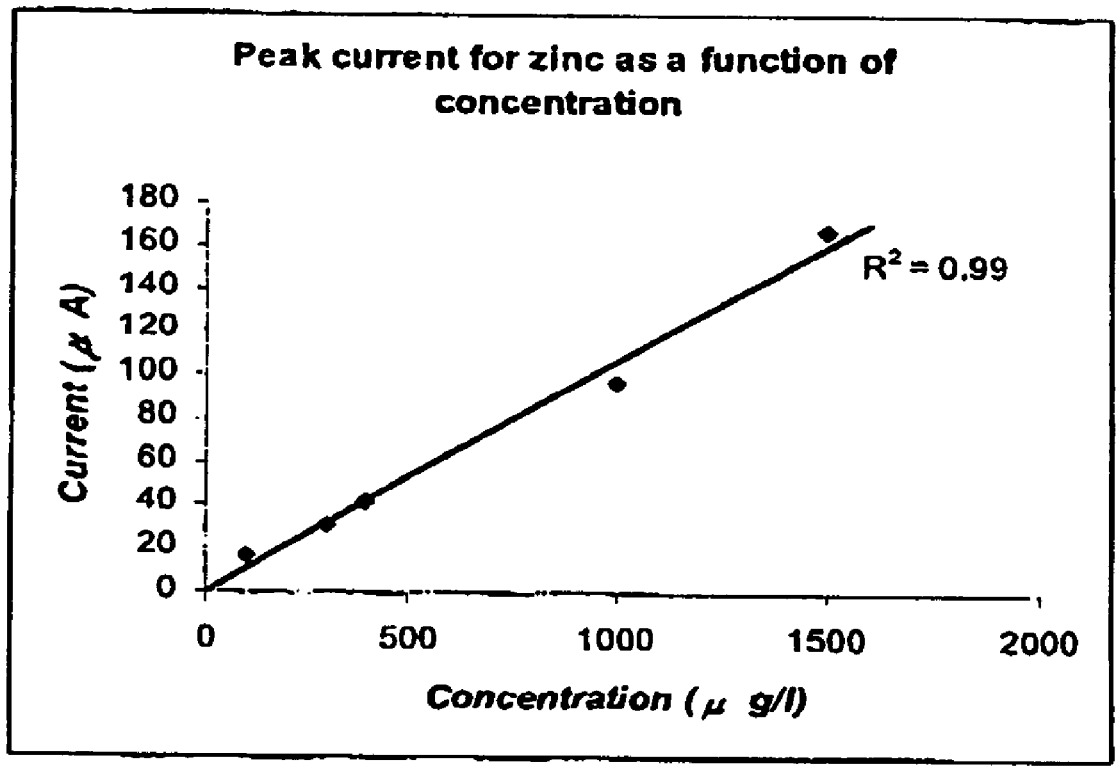
FIG. 5 is a graph showing peak current for zinc as a function of concentration for the experimental conditions in FIG. 4.

As seen in FIG. 4, the addition of zinc resulted in a corresponding increase in the current signal. FIG. 5 shows a plot of the peak current (µA) as a function of zinc concentration (µg/l). The peak current is corrected for a 1.5 µA offset. As shown, there is a good linearity ($R^2=0.99$) between the variables. The experimental conditions were as in FIG. 4.

The results obtained in this section prove that zinc can be detected on the dental amalgam electrode. These results also indicate that an analogous situation will appear for other heavy metals, like cadmium, lead and copper.

The reproducibility was investigated by performing two parallels and is shown in Table 1. Table 1 shows analyses of zinc on dental amalgam electrode, two parallels. The table shows the current values (corrected for offset) obtained in each parallel. Also the average response, the standard deviation and the relative standard deviation are listed in the table.

TABLE 1

| Concentration µg/l | Response µA | Response µA | Avg. resp. µA | Std. deviation µA | Relative std. deviation (%) |
|---|---|---|---|---|---|
| 500 | 12.1 | 11.0 | 11.6 | 0.8 | 6.9 |
| 1000 | 22.8 | 20.3 | 21.6 | 1.7 | 8.0 |
| 1500 | 35.7 | 32.2 | 33.9 | 2.5 | 7.3 |

As seen in Table 1, there is a relative standard deviation of about 75%. This is good with a view that the electrode surface of the working electrode only was polish with soft sandpaper.

3. Results from analyses using a dental amalgam with pure silver only as a working electrode in voltammetry.

Figure 6:
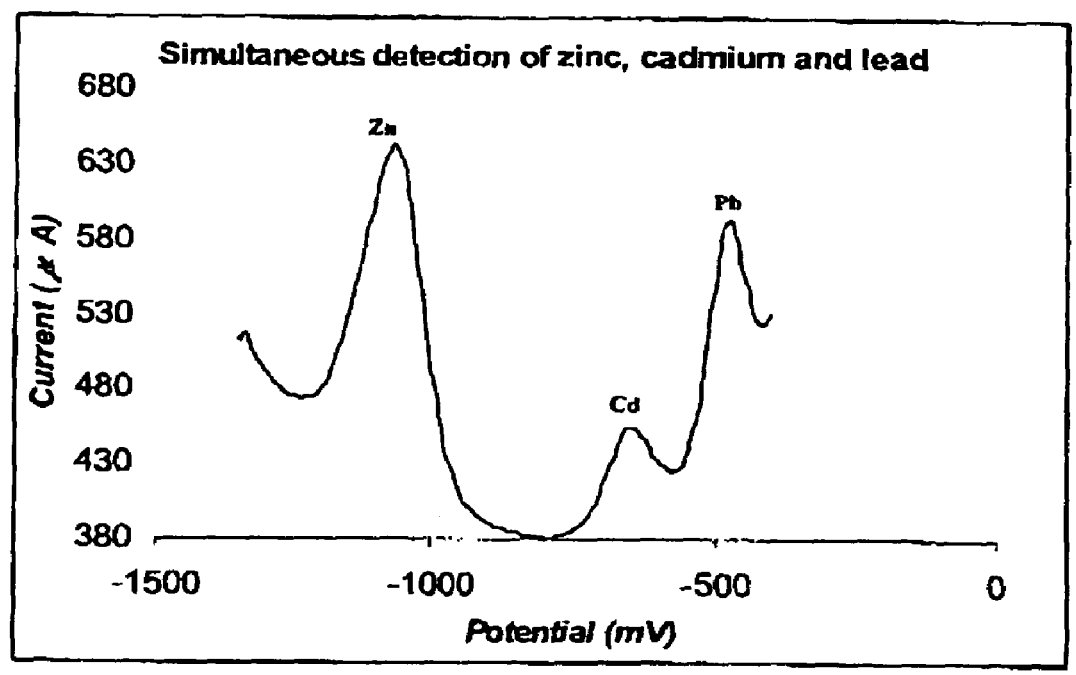
FIG. 6 is a voltammogram of a simultaneous detection of zinc, cadmium and lead.

Some analyses were performed to investigate the use of a pure silver amalgam as a working electrode material. Some simultaneous analyses of zinc, cadmium and lead were performed. The given metals are in the range from 100 µg/l to 150 µg/l in $NH_4Ac$ (0.05 M) solution. Differential pulse anodic stripping voltammetry with a scan rate of 10 mV/sec, pulse height 100 mV, and 180 seconds deposition time was applied. A typical plot of the given voltammogram with current (µA) as a function of potential (mV) is shown in FIG. 6 for the simultaneous detection of 150 µg/l zinc (Zn), 100 µg/l cadmium (Cd) and 100 µg/l lead (Pb) is plotted.

CONCLUSIONS

From the given results it is found that a working electrode consisting of dental amalgam can be used in voltammetry for detection of heavy metals and other species in ppb levels. Further improvements can obviously also be obtained by optimising the composition of the alloy and the electrolyte, and by application of sound to the electrode system (Ref. Patent application 1999 1814, Norway).

Dental amalgam has many properties making it a preferable material for electrode use in voltammetry. It has a high overvoltage against hydrogen and this enables one to determine several compounds which previously could not be determined except by using a mercury electrode. It is a solid material, and this makes it possible to be used in online analyses in the field. It can also be used repeatedly over a long period of time without any maintenance, which is essential for an online and a field apparatus.

The toxicity of dental amalgam is not greater than that people can live with it inside their mouth for a whole life without any poisoning effects, and its use is without any formal environmental restrictions. Also in an electrode the amount of an amalgam will be much lower than the amount used in a tooth filling. Moreover, as no increased amount of mercury is reported in the groundwater close to cemeteries, the use of such small electrodes for soil and groundwater analyses are obviously without any hazard.

Finally, it is easy and cheap to manufacture such electrodes, using techniques well established for dental clinics.

Having described preferred embodiments of the invention it will be apparent to those skilled in the art that other embodiments incorporating the concepts may be used. These and other examples of the invention illustrated above are intended by way of example only and the actual scope of the invention is to be determined from the following claims.

What is claimed is:

1. A method comprising:
   performing voltammetric analysis by using an electrode system comprising at least one electrode,
   wherein a working electrode material of the at least one electrode consists of a silver-mercury amalgam in a solid state.

2. The method according to claim 1, wherein the silver-mercury amalgam comprises one part pure silver crystals for dental use and approximately 0.65 parts analytical grade mercury.

3. The method according to claim 2,
   wherein the electrode system comprises a plurality of electrodes,
   wherein the voltammetric analysis involves a redox reaction at an electrode surface, using an analysis cell and the plurality of electrodes arranged in the analysis cell,
   wherein the analysis cell is filled with a solution to be analyzed through production of a measuring signal as a consequence of the redox reaction, and
   wherein the measuring signal is a measure of the concentration of a component in the solution.

4. The method according to claim 2, wherein the voltammetric analysis is a differential pulse anodic stripping type voltammetry.

5. The method according to claim 4,
   wherein the electrode system comprises a plurality of electrodes,
   wherein the voltammetric analysis involves a redox reaction at an electrode surface, using an analysis cell and the plurality of electrodes arranged in the analysis cell,
   wherein the analysis cell is filled with a solution to be analyzed through production of a measuring signal as a consequence of the redox reaction, and
   wherein the measuring signal is a measure of the concentration of a component in the solution.

6. The method according to claim 1, wherein the voltammetric analysis is a differential pulse anodic stripping type voltammetry.

7. The method according to claim 6,
   wherein the electrode system comprises a plurality of electrodes,
   wherein the voltammetric analysis involves a redox reaction at an electrode surface, using an analysis cell and the plurality of electrodes arranged in the analysis cell,
   wherein the analysis cell is filled with a solution to be analyzed through production of a measuring signal as a consequence of the redox reaction, and
   wherein the measuring signal is a measure of the concentration of a component in the solution.

8. The method according to claim 1,
   wherein the electrode system comprises a plurality of electrodes,
   wherein the voltammetric analysis involves a redox reaction at an electrode surface, using an analysis cell and the plurality of electrodes arranged in the analysis cell,
   wherein the analysis cell is filled with a solution to be analyzed through production of a measuring signal as a consequence of the redox reaction, and
   wherein the measuring signal is a measure of the concentration of a component in the solution.

* * * * *